US006537524B1

(12) United States Patent
Hassan et al.

(10) Patent No.: US 6,537,524 B1
(45) Date of Patent: Mar. 25, 2003

(54) COMBINATIONS OF FORMOTEROL AND A TIOTROPIUM SALT

(75) Inventors: Ian Francis Hassan, Morris Plains, NJ (US); Jeremy Guy Clarke, Bath (GB); Bernard Cuenoud, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/924,246

(22) Filed: Aug. 8, 2001

Related U.S. Application Data

(63) Continuation of application No. PCT/EP00/00958, filed on Feb. 7, 2000.

(30) Foreign Application Priority Data

Feb. 8, 1999 (GB) .............................. 9902689

(51) Int. Cl.$^7$ ............................ A61K 9/12; A61K 9/14; A61K 9/08
(52) U.S. Cl. ......................... 424/45; 424/46; 424/489; 128/200.14; 128/266; 514/630; 514/826; 514/56; 564/216; 564/220
(58) Field of Search ........................... 424/45, 46, 489; 514/630, 56, 23, 826; 564/216, 220; 128/200.14, 266

(56) References Cited

U.S. PATENT DOCUMENTS

| 5,603,918 A | 2/1997 | McNamara ................. 424/46 |
| 5,955,058 A | * 9/1999 | Jager et al. ................ 424/45 |
| 6,150,418 A | 11/2000 | Hochrainer et al. ........ 514/630 |

FOREIGN PATENT DOCUMENTS

| AU | 199856496 B2 | 8/1998 |
| WO | WO 95/05805 | 3/1995 |
| WO | WO 98/34595 | 8/1998 |
| WO | WO 00/07567 | 2/2000 |
| WO | WO 00/16814 | 3/2000 |
| WO | 19847970 | 4/2000 |

OTHER PUBLICATIONS

Barnes, et al., "Tiotropium Bromide (Ba 679 BR), a Novel, Long–Acting Muscarinic Antagonists for the Treatment of Obstructive Airways Disease," Life Sciences, 56:(11/12):853–859 (1995) (Elsevier Science, Ltd., Editors).*
Barnes, "Chronic Obstructive Pulmonary Disease: New Opportunities for Drug Development", TIPS, vol. 19, pp. 415–423 (1998).
Gross, "How to Effectively Control Your Patient's Dyspnea. COPD Management: Achieving Bronchodilation.", J. Respir. Dis., vol. 17, No. 3, pp. 183–195 (1996).
Rees, "Chapter 12. Bronchodilators in the Therapy of Chronic Obstructive Pulmonary Disease.", Guy's and St Thomas' Hospitals, London SE1 9RT, United Kingdom. 14 pages.
Leckie et al., "Novel Therapy for COPD", Exp. Opin. Invest. Drugs, vol. 9, No. 1, pp. 3–23 (2000). (XP–000911149).
Derwent Abstract 2000–195437/17, Keller et al., WO 200007567A1, Feb. 17, 2000.

* cited by examiner

*Primary Examiner*—Michael G. Hartley
*Assistant Examiner*—M. Haghighatian
(74) *Attorney, Agent, or Firm*—Carol A. Loeschorn; D. Gabrielle Brouillette

(57) ABSTRACT

A medicament containing, separately or together, (A) formoterol or a pharmaceutically acceptable salt thereof or a solvate of formoterol or said salt and (B) a tiotropium salt of a pharmaceutically acceptable acid, for simultaneous, sequential or separate administration in the treatment of an inflammatory or obstructive airways disease.

20 Claims, No Drawings

COMBINATIONS OF FORMOTEROL AND A TIOTROPIUM SALT

This is a continuation of International Application No. PCT/EP00/00958, filed Feb. 7, 2000, the contents of which are incorporated herein by reference.

This invention relates to combinations of formoterol and a tiotropium salt and their use for the treatment of inflammatory or obstructive airways diseases.

Formoterol,N-[2-hydroxy-5-(1-hydroxy-2-((2-(4-methoxyphenyl)-1-methylethyl)amino)-ethyl)phenyl] formamide, particularly in the form of its fumarate salt, is a bronchodilator used in the treatment of inflammatory or obstructive airways diseases. Use of tiotropium bromide, $(1\alpha,2\beta,5\alpha,7\beta)$-7-((hydroxydi-2-thienylacetyl)oxy)-9,9-dimethyl-3-oxa-9-azonia-tricyclo$(3.3.1.0^{2,4})$-nonane bromide, in the treatment of chronic obstructive bronchitis is described in U.S. Pat. No. 5,610,163. It has now surprisingly been found that a significant unexpected therapeutic benefit, particularly a synergistic therapeutic benefit, in the treatment of inflammatory or obstructive airways diseases can be obtained by combination therapy using formoterol, or a salt or solvate thereof, and a tiotropium salt. For instance, it is possible using this combination therapy to reduce the dosages required for a given therapeutic effect considerably compared with those required using treatment with formoterol or a tiotropium salt alone, thereby minimising possibly undesirable side effects.

In a further aspect, this combination therapy exhibits both a fast onset of action and a long duration of action, so that patients feel a rapid improvement in their condition and, in view of the long duration of action, a reduced need for short-acting rescue medicaments, such as salbutamol or terbutaline. Surprisingly this effect is exhibited even when the two drugs are administered at the same time, i.e. in a composition containing both drugs or sequentially, so that medicaments of the invention facilitate the treatment of inflammatory or obstructive airways diseases with a medicament which need be administered only once a day. Where necessary, medicaments of the invention can be used on demand in rescue treatment of obstructive or inflammatory airways diseases, so that they facilitate treatment of such diseases with a single medicament.

In one aspect, the present invention provides a medicament containing, separately or together, (A) formoterol or a pharmaceutically acceptable salt thereof or a solvate of formoterol or said salt and (B) a tiotropium salt of a pharmaceutically acceptable acid, for simultaneous, sequential or separate administration in the treatment of an inflammatory or obstructive airways disease.

In another aspect, the present invention provides a method of treating an inflammatory or obstructive airways disease which comprises administering to a subject in need of such treatment effective amounts of (A) as hereinbefore defined and (B) as hereinbefore defined.

In a further aspect, the present invention provides a pharmaceutical composition comprising a mixture of effective amounts of (A) as hereinbefore defined and (B) as hereinbefore defined, optionally together with a pharmaceutically acceptable carrier.

The present invention also provides (A) and (B) as hereinbefore defined for use in combination therapy by simultaneous, sequential or separate administration in the treatment of an inflammatory or obstructive airways disease.

The invention further provides the use of (A) as hereinbefore defined or (B) as hereinbefore defined in the preparation of a medicament for combination therapy by simultaneous, sequential or separate administration of (A) and (B) in the treatment of an inflammatory or obstructive airways disease.

The present invention still further provides the use of (A) and (B) as hereinbefore defined for the preparation of a medicament for combination therapy by simultaneous, sequential or separate administration in the treatment of an inflammatory or obstructive airways disease.

Pharmaceutically acceptable salts of formoterol include, for example, salts of inorganic acids such as hydrochloric, hydrobromic, sulfuric and phosphoric acids, and organic acids such as fumaric, maleic, acetic, lactic, citric, tartaric, ascorbic, succinic, glutaric, gluconic, tricarballylic, oleic, benzoic, p-methoxybenzoic, salicylic, o- and p-hydroxybenzoic, p-chlorobenzoic, methanesulfonic, p-toluenesulfonic and 3-hydroxy-2-naphthalene carboxylic acids.

Component (A) may be in any isomeric form or mixture of isomeric forms, for example a pure enantiomer, a mixture of enantiomers, a racemate or a mixture thereof. It may be in the form of a solvate, for example a hydrate, thereof, for example as described in U.S. Pat. No. 3,994,974 or U.S. Pat. No. 5,684,199, and may be present in a particular crystalline form, for example as described in WO95/05805. Preferably, component (A) is formoterol fumarate, especially in the form of the dihydrate.

The tiotropium salt (B) is preferably tiotropium methanesulfonate or, especially, tiotropium bromide,$(1\alpha,2\beta,4\beta,5\alpha,7\beta)$-7-((hydroxydi-2-thienylacetyl)oxy)-9,9-dimethyl-3-oxa-9-azoniatricyclo$(3.3.1.0^{2,4})$-nonane bromide, the preparation of which is described in U.S. Pat. No. 5,610,163.

Administration of the medicament or pharmaceutical composition as hereinbefore described, i.e. with (A) and (B) in admixture or separate, is preferably by inhalation, i.e. (A) and (B) or the mixture thereof are in inhalable form. The inhalable form of the medicament i.e. of (A) and/or (B) may be, for example, an atomizable composition such as an aerosol comprising the active ingredient, i.e. (A) and (B) separately or in admixture, in solution or dispersion in a propellant, or a nebulizable composition comprising a dispersion of the active ingredient in an aqueous, organic or aqueous/organic medium. For example, the inhalable form of the medicament may be an aerosol comprising a mixture of (A) and (B) in solution or dispersion in a propellant, or a combination of an aerosol containing (A) in solution or dispersion in a propellant with an aerosol containing (B) in solution or dispersion in a propellant. In another example, the inhalable form is a nebulizable composition comprising a dispersion of (A) and (B) in an aqueous, organic or aqueous/organic medium, or a combination of a dispersion of (A) in such a medium with a dispersion of (B) in such a medium.

An aerosol composition suitable for use as the inhalable form of the medicament may comprise the active ingredient in solution or dispersion in a propellant, which may be chosen from any of the propellants known in the art. Suitable such propellants include hydrocarbons such as n-propane, n-butane or isobutane or mixtures of two or more such hydrocarbons, and halogen-substituted hydrocarbons, for example fluorine-substituted methanes, ethanes, propanes, butanes, cyclopropanes or cyclobutanes, particularly 1,1,1,2-tetrafluoroethane (HFA134a) and 1,1,1,2,3,3,3-heptafluoropropane (HFA227), or mixtures of two or more such halogen-substituted hydrocarbons. Where the active ingredient is present in suspension in the propellant, i.e. where it is present in particulate form dispersed in the propellant, the aerosol composition may also contain a lubricant and a surfactant, which may be chosen from those lubricants and surfactants known in the art. Other suitable aerosol compositions include surfactant-free or substantially surfactant-free aerosol compositions. The aerosol composition may contain up to about 5% by weight, for example 0.002 to 5%, 0.01 to 3%, 0.015 to 2%, 0.1 to 2%, 0.5 to 2% or 0.5 to 1%, by weight of the active ingredient, based on the weight of the propellant. Where present, the lubricant and surfactant may be in an amount up to 5% and 0.5% respectively by weight of the aerosol composition. The aerosol composition may also contain a co-solvent such as ethanol in an amount up to 30% by weight of the composition, particularly for administration from a pressurised metered dose inhalation device.

In another embodiment of the invention, the inhalable form is a dry powder, i.e. (A) and/or (B) are present in a dry powder comprising finely divided (A) and/or (B) optionally together with a finely divided pharmaceutically acceptable carrier, which is preferably present and may be chosen from materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran or mannitol. An especially preferred carrier is lactose. The dry powder may be in capsules of gelatin or plastic, or in blisters, for use in a dry powder inhalation device, preferably in dosage units of 1 μg to 140 μg of the active ingredient. Alternatively, the dry powder may be contained as a reservoir in a multi-dose dry powder inhalation device.

In the finely divided particulate form of the medicament, and in the aerosol composition where the active ingredient is present in particulate form, the active ingredient may have an average particle diameter of up to about 10 μm, for example 0.1 to 5 μm, preferably 1 to 5 μm. The finely divided carrier, where present, generally has a maximum particle diameter up to 300 μm, preferably up to 212 μm and conveniently has a mean particle diameter of 40 to 100 μm, preferably 50 to 75 μm. The particle size of the active ingredient, and that of the carrier where present in dry powder compositions, can be reduced to the desired level by conventional methods, for example by grinding in an air-jet mill, ball mill or vibrator mill, microprecipitation, spray-drying, lyophilisation or recrystallisation from supercritical media.

The inhalable medicament may be administered using an inhalation device suitable for the inhalable form, such devices being well known in the art. Accordingly, the invention also provides a pharmaceutical product comprising a medicament or pharmaceutical composition as hereinbefore described in inhalable form as hereinbefore described in association with one or more inhalation devices. In a further aspect, the invention provides an inhalation device, or a pack of two or more inhalation devices, containing a medicament or pharmaceutical composition as hereinbefore described in inhalable form as hereinbefore described.

Where the inhalable form of the active ingredient is an aerosol composition, the inhalation device may be an aerosol vial provided with a valve adapted to deliver a metered dose, such as 10 to 100 μl, e.g. 25 to 50 μl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, for example an electronically controlled device such as an AERx (ex Aradigm, US) or a mechanical device such as a RESPIMAT (Boehringer Ingelheim) nebulizer which allows much smaller nebulized volumes, e.g. 10 to 100 μl, than conventional nebulizers. Where the inhalable form of the active ingredient is the finely divided particulate form, the inhalation device may be, for example, a dry powder inhalation device adapted to deliver dry powder from a capsule or blister containing dry powder comprising a dosage unit of (A) and/or (B), or a multidose dry powder inhalation (MDPI) device adapted to deliver, for example, 5–25 mg of dry powder comprising a dosage unit of (A) and/or (B) per actuation. Suitable such dry powder inhalation devices are well known. For example, a suitable device for delivery of dry powder in encapsulated form is that described in U.S. Pat. No. 3,991,761, while a suitable MDPI device is that described in WO097/20589.

The medicament of the invention is preferably a pharmaceutical composition comprising a mixture of (A) as hereinbefore defined and (B) as hereinbefore defined, preferably together with a pharmaceutically acceptable carrier as hereinbefore described.

The weight ratio of formoterol, or salt or solvate thereof, to tiotropium salt may be, in general, from 72:1 to 1:160, for example from 72:1 to 1:120, from 72:1 to 1:80, from 60:1 to 1:80, from 60:1 to 1:70, from 50:1 to 1:60, from 60:1 to 1:50, from 50:1 to 1:50, from 60:1 to 1:40, from 50:1 to 1:40, from 50:1 to 1:30, from 50:1 to 1:20, from 50:1 to 1:30, from 50:1 to 1:20, from 50:1 to 1:10, from 40:1 to 1:20, from 40:1 to 1:10, from 30:1 to 1:20, from 30:1 to 1:10, from 20:1 to 1:20, from 20:1 to 1:10, from 20:1 to 1:5, from 16:1 to 1:4, from 10:1 to 1:5, from 6:1 to 1:4, or from 4:1 to 1:3. More usually, this ratio is from 3:1 to 1:3, for example from 2.5:1 to 1:2, from 2:1 to 1:2, from 1.5:1 to 1:1.5, or from 1.5:1 to 1:1.2. The two drugs may be administered separately in the same ratio. Specific examples of this ratio include 3:1, 2.9:1, 2.8:1, 2.7:1. 2.6:1. 2.5:1. 2.4:1, 2.3:1, 2.2:1, 2.1:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9 and 1:2. The above weight ratios apply particularly where (A) is formoterol fumarate dihydrate and (B) is tiotropium bromide. Thus, since the molecular weights of formoterol fumarate dihydrate and tiotropium bromide are 840.9 and 472.4 respectively, the corresponding molar ratios, which apply to any forms of (A) and (B), can be readily calculated. For instance, the above weight ratios of 60:1 and 1:80 correspond to molar ratios of 33.7:1 and 1:142.3 respectively.

A suitable daily dose of formoterol, or salt or solvate thereof, particularly as formoterol fumarate dihydrate, for inhalation may be from 1 to 72 μg, for example from 1 to 60 μg, generally from 3 to 50 μg, preferably from 6 to 48 μg, for instance from 6 to 24 μg. A suitable daily dose of tiotropium salt, particularly as tiotropium bromide, for inhalation may be from 1 to 160 μg, for example from 1 to 120 μg, from 1 to 80 μg, from 1 to 70 μg, from 1 to 60 μg, from 1 to 50 μg, from 1 to 40 μg, from 1 to 25 μg, preferably from 3 to 36 μg, for instance from 9 to 36 μg. The precise dose used will of course depend on the condition to be treated, the patient and the efficiency of the inhalation device. The unit doses of (A) and (B) and their frequency of administration may be chosen accordingly. A suitable unit dose of formoterol component (A), particularly as formoterol fumarate dihydrate, may be from 1 to 72 μg, for example from 1 to 60 μg, generally from 3 to 48 μg, preferably from 6 to 36 μg, especially from 12 to 24 μg. A suitable unit dose of tiotropium salt (B), particularly as tiotropium bromide, may be from 1 μg to 80 μg, for example from 1 μg to 50 μg, preferably from 3 μg to 36 μg, especially from 9 to 36 μg. These unit doses may suitably be administered once or twice daily in accordance with the suitable daily dose mentioned hereinbefore. For on demand usage, unit doses of 6 μg to 12 μg of (A) and 3 μg to 36 μg of (B) are preferred.

In one preferred embodiment of the invention, when the medicament of the invention is a pharmaceutical composition which is a dry powder in capsules containing a unit dose of (A) and (B), for example for inhalation from a single capsule inhaler, the capsules may suitably contain, where (A) is formoterol fumarate dihydrate, and (B) is tiotropium bromide, from 3 µg to 36 µg of (A), preferably from 6 µg to 24 µg of (A), especially from 12 µg to 24 µg of (A), and from 3 µg to 80 µg of (B), preferably from 5 µg to 50 µg of (B), especially from 9 to 36 µg of (B), together with a pharmaceutically acceptable carrier as hereinbefore described in an amount to bring the total weight of dry powder per capsule to between 5 mg and 50 mg, for example 5 mg, 10 mg, 15 mg, 20 mg, 25 mg, 30 mg, 35 mg, 40 mg, 45 mg or 50 mg, preferably 20 to 25 mg, especially 25 mg.

In another preferred embodiment of the invention, the medicament of the invention is a pharmaceutical composition which is a dry powder for administration from a reservoir of a multi-dose dry powder inhaler adapted to deliver 3 mg to 25 mg of powder containing a unit dose of (A) and (B) per actuation, for example, where (A) is formoterol fumarate dihydrate, and (B) is tiotropium bromide, a powder comprising, by weight, 3 to 36 parts, preferably 6 to 24 parts, especially 12 to 24 parts of (A); 3 to 80 parts, preferably 5 to 50 parts, especially 9 to 36 parts of (B); and 2884 to 24994 parts, preferably 4884 to 14994 parts, especially 4884 to 9994 parts of a pharmaceutically acceptable carrier as hereinbefore described.

In accordance with the above, the invention also provides a pharmaceutical kit comprising (A) and (B) as hereinbefore defined in separate unit dosage forms, said forms being suitable for administration of (A) and (B) in effective amounts. Such a kit suitably further comprises one or more inhalation devices for administration of (A) and (B). For example, the kit may comprise one or more dry powder inhalation devices adapted to deliver dry powder from a capsule, together with capsules containing a dry powder comprising a dosage unit of (A) and capsules containing a dry powder comprising a dosage unit of (B). In another example, the kit may comprise a multidose dry powder inhalation device containing in the reservoir thereof a dry powder comprising (A) and a multidose dry powder inhalaiton device containing in the reservoir thereof a dry powder comprising (B). In a further example, the kit may comprise a metered dose inhaler containing an aerosol comprising comprising (A) in a propellant and a metered dose inhaler containing an aerosol comprising (B) in a propellant.

Treatment of inflammatory or obstructive airways diseases in accordance with the invention may be symptomatic or prophylactic treatment. Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), acute respiratory distress syndrome (ARDS), chronic obstructive pulmonary, airways or lung disease (COPD, COAD or COLD), including chronic bronchitis and emphysema, bronchiectasis and exacerbation of airways hyperreactivity consequent to other drug therapy, in particular other inhaled drug therapy. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

The invention is illustrated by the following Examples, in which parts are by weight unless stated otherwise.

EXAMPLE 1

Aerosol Composition for Metered Dose Inhaler

| Ingredient | % by weight |
| --- | --- |
| Formoterol fumarate dihydate | 0.01 |
| Tiotropium bromide | 0.01 |
| Ethanol (absolute) | 2.50 |
| HFA 227 | 60.92 |
| HFA134a | 36.56 |

EXAMPLE 2

Dry Powder

| Ingredient | % by weight |
| --- | --- |
| Formoterol fumarate dihydate | 0.05 |
| Tiotropium bromide | 0.05 |
| Lactose Monohydrate | 99.90 |

EXAMPLE 3

A dry powder suitable for delivery from the reservoir of the multi-dose inhaler described in WO97/20589 is prepared by mixing 12 parts of formoterol fumarate dihydrate which has been ground to a mean particle diameter of 1–5 µm in an air-jet mill, 18 parts of tiotropium bromide which has been similarly ground to a mean particle diameter of 1–5 µm and 4970 parts of lactose monohydrate having a particle diameter below 212 µm.

EXAMPLES 4–92

Example 3 is repeated, but using the amounts of the ingredients shown in the table below in place of the amounts used in that Example:

| Example | Formoterol Fumarate Dihydrate (Parts) | Tiotropium Bromide (Parts) | Lactose Monohydrate (Parts) |
| --- | --- | --- | --- |
| 4 | 12 | 3 | 4985 |
| 5 | 12 | 9 | 4979 |
| 6 | 12 | 36 | 4952 |
| 7 | 12 | 80 | 4908 |
| 8 | 6 | 3 | 4991 |
| 9 | 6 | 9 | 4985 |
| 10 | 6 | 18 | 4976 |
| 11 | 6 | 36 | 4958 |
| 12 | 6 | 80 | 4914 |
| 13 | 18 | 3 | 4979 |
| 14 | 18 | 9 | 4973 |
| 15 | 18 | 18 | 4964 |
| 16 | 18 | 36 | 4946 |
| 17 | 18 | 80 | 4902 |
| 18 | 24 | 3 | 4973 |
| 19 | 24 | 9 | 4967 |
| 20 | 24 | 18 | 4958 |
| 21 | 24 | 36 | 4940 |
| 22 | 24 | 80 | 4896 |
| 23 | 30 | 3 | 4967 |
| 24 | 30 | 9 | 4961 |
| 25 | 30 | 18 | 4952 |
| 26 | 30 | 36 | 4934 |
| 27 | 30 | 80 | 4890 |
| 28 | 36 | 3 | 4961 |
| 29 | 36 | 9 | 4955 |
| 30 | 36 | 18 | 4946 |
| 31 | 36 | 36 | 4928 |
| 32 | 36 | 80 | 4884 |
| 33 | 6 | 3 | 9991 |
| 34 | 6 | 9 | 9985 |
| 35 | 6 | 18 | 9976 |
| 36 | 6 | 36 | 9958 |
| 37 | 6 | 80 | 9914 |
| 38 | 12 | 3 | 9985 |
| 39 | 12 | 9 | 9979 |
| 40 | 12 | 18 | 9970 |
| 41 | 12 | 36 | 9952 |
| 42 | 12 | 80 | 9908 |
| 43 | 18 | 3 | 9979 |
| 44 | 18 | 9 | 9973 |
| 45 | 18 | 18 | 9964 |
| 46 | 18 | 36 | 9946 |
| 47 | 18 | 80 | 9902 |
| 48 | 24 | 3 | 9973 |
| 49 | 24 | 9 | 9967 |
| 50 | 24 | 18 | 9958 |
| 51 | 24 | 36 | 9940 |
| 52 | 24 | 80 | 9896 |
| 53 | 30 | 3 | 9967 |
| 54 | 30 | 9 | 9961 |
| 55 | 30 | 18 | 9952 |
| 56 | 30 | 36 | 9934 |
| 57 | 30 | 80 | 9890 |
| 58 | 36 | 3 | 9961 |
| 59 | 36 | 9 | 9955 |
| 60 | 36 | 18 | 9946 |
| 61 | 36 | 36 | 9928 |
| 62 | 36 | 80 | 9884 |
| 63 | 6 | 3 | 14991 |
| 64 | 6 | 9 | 14985 |
| 65 | 6 | 18 | 14976 |
| 66 | 6 | 36 | 14958 |
| 67 | 6 | 80 | 14914 |
| 68 | 12 | 3 | 14985 |
| 69 | 12 | 9 | 14979 |
| 70 | 12 | 18 | 14970 |
| 71 | 12 | 36 | 14952 |
| 72 | 12 | 80 | 14908 |
| 73 | 18 | 3 | 14979 |
| 74 | 18 | 9 | 14973 |
| 75 | 18 | 18 | 14964 |
| 76 | 18 | 36 | 14946 |
| 77 | 18 | 80 | 14902 |
| 78 | 24 | 3 | 14973 |
| 79 | 24 | 9 | 14967 |
| 80 | 24 | 18 | 14958 |
| 81 | 24 | 36 | 14940 |
| 82 | 24 | 80 | 14896 |
| 83 | 30 | 3 | 14967 |
| 84 | 30 | 9 | 14961 |
| 85 | 30 | 18 | 14952 |
| 86 | 30 | 36 | 14934 |
| 87 | 30 | 80 | 14890 |
| 88 | 36 | 3 | 14961 |
| 89 | 36 | 9 | 14955 |
| 90 | 36 | 18 | 14946 |
| 91 | 36 | 36 | 14928 |
| 92 | 36 | 80 | 14884 |

EXAMPLE 93

Gelatin capsules suitable for use in a capsule inhaler such as that described in U.S. Pat. No. 3,991,761 are prepared, each capsule containing a dry powder obtained by mixing 12 μg of formoterol fumarate dihydrate which has been ground to a mean particle diameter of 1 to 5 μm in an air jet mill, 18 μg of tiotropium bromide which has been similarly ground to a mean particle diameter of 1 to 5 μm and 24970 μg of lactose monohydrate having a particle diameter below 212 μm.

EXAMPLES 94–152

Example 93 is repeated, but using the amounts of the ingredients shown in the table below in place of the amounts used in that Example:

| Example | Formoterol Fumarate Dihydrate (Parts) | Tiotropium Bromide (Parts) | Lactose Monohydrate (Parts) |
| --- | --- | --- | --- |
| 94 | 12 | 3 | 24985 |
| 95 | 12 | 9 | 24979 |
| 96 | 12 | 36 | 24952 |
| 97 | 12 | 80 | 24908 |
| 98 | 6 | 3 | 24991 |
| 99 | 6 | 9 | 24985 |
| 100 | 6 | 18 | 24976 |
| 101 | 6 | 36 | 24958 |
| 102 | 6 | 80 | 24914 |
| 103 | 18 | 3 | 24979 |
| 104 | 18 | 9 | 24973 |
| 105 | 18 | 18 | 24964 |
| 106 | 18 | 36 | 24946 |
| 107 | 18 | 80 | 24902 |
| 108 | 24 | 3 | 24973 |
| 109 | 24 | 9 | 24967 |
| 110 | 24 | 18 | 24958 |
| 111 | 24 | 36 | 24940 |
| 112 | 24 | 80 | 24896 |
| 113 | 30 | 3 | 24967 |
| 114 | 30 | 9 | 24961 |
| 115 | 30 | 18 | 24952 |
| 116 | 30 | 36 | 24934 |
| 117 | 30 | 80 | 24890 |
| 118 | 36 | 3 | 24961 |
| 119 | 36 | 9 | 24955 |
| 120 | 36 | 18 | 24946 |

| Example | Formoterol Fumarate Dihydrate (Parts) | Tiotropium Bromide (Parts) | Lactose Monohydrate (Parts) |
|---|---|---|---|
| 121 | 36 | 36 | 24928 |
| 122 | 36 | 80 | 24884 |
| 123 | 6 | 3 | 19991 |
| 124 | 6 | 9 | 19985 |
| 125 | 6 | 18 | 19976 |
| 126 | 6 | 36 | 19958 |
| 127 | 6 | 80 | 19914 |
| 128 | 12 | 3 | 19985 |
| 129 | 12 | 9 | 19979 |
| 130 | 12 | 18 | 19970 |
| 131 | 12 | 36 | 19952 |
| 132 | 12 | 80 | 19908 |
| 133 | 18 | 3 | 19979 |
| 134 | 18 | 9 | 19973 |
| 135 | 18 | 18 | 19964 |
| 136 | 18 | 36 | 19946 |
| 137 | 18 | 80 | 19902 |
| 138 | 24 | 3 | 19973 |
| 139 | 24 | 9 | 19967 |
| 140 | 24 | 18 | 19958 |
| 141 | 24 | 36 | 19940 |
| 142 | 24 | 80 | 19896 |
| 143 | 30 | 3 | 19967 |
| 144 | 30 | 9 | 19961 |
| 145 | 30 | 18 | 19952 |
| 146 | 30 | 36 | 19934 |
| 147 | 30 | 80 | 19890 |
| 148 | 36 | 3 | 19961 |
| 149 | 36 | 9 | 19955 |
| 150 | 36 | 18 | 19946 |
| 151 | 36 | 36 | 19928 |
| 152 | 36 | 80 | 19884 |

EXAMPLES 153–216

Example 3 is repeated, but using the amounts of the ingredients shown in the table below in place of the amounts used in that Example:

| Example | Formoterol Fumarate Dihydrate (Parts) | Tiotropium Bromide (Parts) | Lactose Monohydrate (Parts) |
|---|---|---|---|
| 153 | 6 | 3 | 2991 |
| 154 | 6 | 9 | 2985 |
| 155 | 6 | 18 | 2976 |
| 156 | 6 | 25 | 2969 |
| 157 | 6 | 36 | 2958 |
| 158 | 6 | 80 | 2914 |
| 159 | 12 | 3 | 2985 |
| 160 | 12 | 9 | 2979 |
| 161 | 12 | 18 | 2970 |
| 162 | 12 | 25 | 2963 |
| 163 | 12 | 36 | 2952 |
| 164 | 12 | 45 | 2943 |
| 165 | 12 | 60 | 2928 |
| 166 | 12 | 72 | 2916 |
| 167 | 12 | 80 | 2908 |
| 168 | 24 | 3 | 2973 |
| 169 | 24 | 9 | 2967 |
| 170 | 24 | 18 | 2958 |
| 171 | 24 | 25 | 2951 |
| 172 | 24 | 36 | 2940 |
| 173 | 24 | 45 | 2931 |
| 174 | 24 | 60 | 2916 |
| 175 | 24 | 72 | 2904 |
| 176 | 24 | 80 | 2896 |
| 177 | 6 | 25 | 4969 |
| 178 | 6 | 45 | 4949 |
| 179 | 6 | 60 | 4934 |
| 180 | 6 | 72 | 4922 |
| 181 | 12 | 25 | 4963 |
| 182 | 12 | 45 | 4943 |
| 183 | 12 | 60 | 4928 |
| 184 | 12 | 72 | 4916 |
| 185 | 24 | 25 | 4951 |
| 186 | 24 | 45 | 4931 |
| 187 | 24 | 60 | 4916 |
| 188 | 24 | 72 | 4904 |
| 189 | 6 | 25 | 9969 |
| 190 | 6 | 45 | 9949 |
| 191 | 6 | 60 | 9934 |
| 192 | 6 | 72 | 9922 |
| 193 | 12 | 25 | 9963 |
| 194 | 12 | 45 | 9943 |
| 195 | 12 | 60 | 9928 |
| 196 | 12 | 72 | 9916 |
| 197 | 24 | 25 | 9951 |
| 198 | 24 | 45 | 9931 |
| 199 | 24 | 60 | 9916 |
| 200 | 24 | 72 | 9904 |
| 201 | 6 | 25 | 14969 |
| 202 | 6 | 45 | 14949 |
| 203 | 6 | 60 | 14934 |
| 204 | 6 | 72 | 14922 |
| 205 | 12 | 25 | 14963 |
| 206 | 12 | 45 | 14943 |
| 207 | 12 | 60 | 14928 |
| 208 | 12 | 72 | 14916 |
| 209 | 24 | 25 | 14951 |
| 210 | 24 | 45 | 14931 |
| 211 | 24 | 60 | 14916 |
| 212 | 24 | 72 | 14904 |
| 213 | 24 | 90 | 14886 |
| 214 | 24 | 108 | 14868 |
| 215 | 24 | 135 | 14841 |
| 216 | 24 | 160 | 14816 |

EXAMPLES 217–256

Example 93 is repeated, but using the amounts of the ingredients shown in the table below in place of the amounts used in that Example:

| Example | Formoterol Fumarate Dihydrate ($\mu$g) | Tiotropium Bromide ($\mu$g) | Lactose Monohydrate ($\mu$g) |
|---|---|---|---|
| 217 | 6 | 3 | 14991 |
| 218 | 6 | 9 | 14985 |
| 219 | 6 | 18 | 14976 |
| 220 | 6 | 25 | 14969 |
| 221 | 6 | 36 | 14958 |
| 222 | 6 | 45 | 14949 |
| 223 | 6 | 60 | 14934 |
| 224 | 6 | 72 | 14922 |
| 225 | 6 | 80 | 14914 |
| 226 | 12 | 3 | 14985 |
| 227 | 12 | 9 | 14979 |
| 228 | 12 | 18 | 14970 |
| 229 | 12 | 25 | 14963 |
| 230 | 12 | 36 | 14952 |
| 231 | 12 | 45 | 14943 |
| 232 | 12 | 60 | 14928 |

-continued

| Example | Formoterol Fumarate Dihydrate (µg) | Tiotropium Bromide (µg) | Lactose Monohydrate (µg) |
|---|---|---|---|
| 233 | 12 | 72 | 14916 |
| 234 | 12 | 80 | 14908 |
| 235 | 12 | 160 | 14828 |
| 236 | 24 | 3 | 14973 |
| 237 | 24 | 9 | 14967 |
| 238 | 24 | 18 | 14958 |
| 239 | 24 | 25 | 14951 |
| 240 | 24 | 36 | 14940 |
| 241 | 24 | 45 | 14931 |
| 242 | 24 | 80 | 14896 |
| 243 | 6 | 3 | 9991 |
| 244 | 6 | 9 | 9985 |
| 245 | 6 | 18 | 9976 |
| 246 | 6 | 25 | 9969 |
| 247 | 6 | 36 | 9958 |
| 248 | 6 | 45 | 9949 |
| 249 | 6 | 80 | 9914 |
| 250 | 12 | 3 | 9985 |
| 251 | 12 | 9 | 9979 |
| 252 | 12 | 18 | 9970 |
| 253 | 12 | 25 | 9963 |
| 254 | 12 | 36 | 9952 |
| 255 | 12 | 45 | 9943 |
| 256 | 12 | 80 | 9908 |

What is claimed is:

1. A medicament containing, separately or together, (A) formoterol or a pharmaceutically acceptable salt thereof or a solvate of formoterol or said salt and (B) a tiotropium salt of a pharmaceutically acceptable acid, for simultaneous, sequential or separate administration and wherein (A) and (B) are provided in synergistically effective amounts for the treatment of an inflammatory or obstructive airways disease.

2. A medicament according to claim 1 which is a pharmaceutical composition comprising a mixture of effective amounts of (A) and (B), optionally together with a pharmaceutically acceptable carrier.

3. A medicament according to claim 1, in which (A) is formoterol fumarate dihydrate and (B) is tiotropium bromide.

4. A medicament according to claim 2, in which (A) is formoterol fumarate dihydrate and (B) is tiotropium bromide.

5. A medicament according to claim 1, which is in inhalable form.

6. A medicament according to claim 2, which is in inhalable form.

7. A medicament according to claim 1 which is in inhalable form, said form being an aerosol comprising a mixture of (A) and (B) in solution or dispersion in a propellant, or a combination of an aerosol containing (A) in solution or dispersion in a propellant with an aerosol containing (B) in solution or dispersion in a propellant.

8. A medicament according to claim 7, in which the aerosol comprises 0.002 to 5% by weight (A) and (B) separately or in admixture, based on the weight of the propellant.

9. A medicament according to claim 1 which is inhalable form, said form being a nebulizable composition comprising a dispersion of (A) and (B) in an aqueous, organic or aqueous/organic medium or a combination of a dispersion of (A) in said medium with a dispersion of (B) in said medium.

10. A medicament according to claim 1 which is in inhalable form, said form being a dry powder comprising finely divided (A) and/or (B) optionally together with a pharmaceutically acceptable carrier in finely divided form.

11. A medicament according to claim 10, in which the carrier is present and is a saccharide.

12. A medicament according to claim 11, in which the carrier is lactose.

13. A medicament according to claim 10, in which (A) and/or (B) has an average particle diameter up to 10 µm.

14. A medicament according to claim 2, in which the weight ratio of (A) to (B) is from 72:1 to 1:160.

15. A medicament according to claim 14, in which said ratio is from 60:1 to 1:80.

16. A medicament according to claim 15, in which said ratio is from 3:1 to 1:3.

17. A pharmaceutical composition which is a dry powder in a capsule, the capsule containing from 3 to 36 µg of (A) formoterol fumarate dihydrate, from 3 to 80 µg of (B) tiotropium bromide and a pharmaceutically acceptable carrier in an amount to bring the total weight of dry powder per capsule to between 5 mg and 50 mg for the treatment of an inflammatory or obstructive airways disease.

18. A medicament according to claim 2, which is a dry powder comprising, by weight, 3 to 36 parts of (A) as formoterol fumarate dihydrate, 3 to 80 parts of (B) as tiotropium bromide and 2884 to 24994 parts of a pharmaceutically acceptable carrier.

19. A method of treating an inflammatory or obstructive airways disease which comprises administering to a subject in need of such treatment synergistically effective amounts of (A) formoterol or a pharmaceutically acceptable salt thereof or a solvate of formoterol or said salt and (B) a tiotropium salt of a pharmaceutically acceptable acid.

20. A pharmaceutical kit comprising (A) formoterol or a pharmaceutically acceptable salt thereof or a solvate of formoterol or said salt and (B) a tiotropium salt of a pharmaceutically acceptable acid in separate unit dosage forms, said forms being suitable for administration of (A) and (B) in synergistically effective amounts, together with one or more inhalation devices for administration of (A) and (B).

* * * * *